United States Patent [19]

Miura et al.

[11] Patent Number: 4,773,969

[45] Date of Patent: Sep. 27, 1988

[54] CHLORINE ION-SELECTIVE ELECTRODE

[75] Inventors: Kenji Miura; Takehiko Sato; Osamu Seshimoto, all of Asaka, Japan

[73] Assignee: Fuji Photo Film Co., Ltd., Kanagawa, Japan

[21] Appl. No.: 110,565

[22] Filed: Oct. 19, 1987

[30] Foreign Application Priority Data

Jan. 22, 1986 [JP] Japan .................................. 61-11243

[51] Int. Cl.[4] ...................... G01N 27/30; G01N 27/50
[52] U.S. Cl. ...................................... 204/1 T; 204/418
[58] Field of Search ................................ 204/1 B, 418

[56] References Cited

U.S. PATENT DOCUMENTS

| | | | |
|---|---|---|---|
| 3,740,326 | 6/1973 | Grubb | 204/1 B X |
| 3,801,486 | 4/1974 | Wise | 204/1 B X |
| 4,199,411 | 4/1980 | Kim | 204/1 T |
| 4,199,412 | 4/1980 | Battaglia et al. | 204/1 T |
| 4,214,968 | 7/1980 | Battaglia et al. | 204/195 |
| 4,549,951 | 10/1985 | Knudson et al. | 204/416 |
| 4,597,848 | 7/1986 | Oka et al. | 204/418 |

FOREIGN PATENT DOCUMENTS 157151  9/1982  Japan .................................. 204/418

*Primary Examiner*—G. L. Kaplan
*Attorney, Agent, or Firm*—Jules E. Goldberg

[57] ABSTRACT

In a chlorine ion-selective electrode for analysis of chlorine ion in a liquid sample which comprises a silver metal layer, a silver chloride layer and a chlorine ion-selective membrane, superposed in order, the chlorine ion-selective membrane containing a hydrophobic organic polymer as a binder, the improvement wherein the hydrophobic organic polymer is a vinyl acetal polymer such as vinyl butyral or a copolymer of a vinyl acetal and at least one monomer copolymerizable therewith such as a copolymer of vinyl butyral and vinyl alcohol.

5 Claims, No Drawings

CHLORINE ION-SELECTIVE ELECTRODE

This is a continuation of application Ser. No. 7,133, filed Jan. 22, 1987 and now abandoned.

BACKGROUND OF THE INVENTION

1. Field of the Invention

This invention relates to a chlorine ion-selective electrode employable for quantitative analysis of chlorine ion contained in a liquid sample such as a body fluid.

2. Description of the Prior Art

There are known chlorine ion-selective electrodes comprising a silver metal layer, a silver chloride layer and a chlorine ion-selective membrane, superposed in this order, wherein said chlorine ion-selective membrane contains a hydrophobic organic polymer as a binder. For instance, such chlorine ion-selective electrodes are disclosed in U.S. Pat. No. 3,591,482.

Generally, the chlorine ion-selective membrane comprises a quaternary ammonium salt (e.g., Aliquat 336, tradename, manufactured by Aldrich Chemical, Inc.) and a hydrophobic organic polymer as a binder. As the hydrophobic organic polymer to be used as the binder in the ion-selective membrane, there are known, for instance, vinyl chloride copolymers described in Japanese Patent Provisional Publication No. 58(1983)-156848. However, the vinyl chloride copolymers have disadvantages in that they suffer greatly drift at the initial stage in the measurement of potential and further suffer the interference of co-existing bromine ion. Polyvinyl chlorides proposed as the binder prior to the above-described publication have similar disadvantages. When the drift at the initial stage in the measurement of potential is large, there is caused a problem that the reproducibility of potential to be measured after the lapse of a certain period after the contact of a liquid sample with the electrode becomes poor and hence, reproducibility of the analysis of the chlorine ion concentration becomes poor.

SUMMARY OF THE INVENTION

It is an object of the present invention to provide a chlorine ion-selective electrode which scarcely suffers drift particularly at the initial stage in the measurement of potential, that is, exhibits good reproducibility of the analysis of chlorine ion concentration through the measurement of potential and does not suffer the interference of bromine ion.

There is provided by the present invention an improvement of the chlorine ion-selective electrode comprising a silver metal layer, a silver chloride layer and a chlorine ion-selective membrane, superposed in order, said chlorine ion-selective membrane containing a hydrophobic organic polymer as a binder, wherein said hydrophobic organic polymer is a vinyl acetal polymer or a copolymer of a vinyl acetal and at least one monomer copolymerizable therewith.

DETAILED DESCRIPTION OF THE INVENTION

The silver metal layer and the silver chloride layer can be prepared by various known methods. Nevertheless, the methods described in Japanese Patent Provisional Publication Nos. 56(1981)-33537 and 57(1982)-186163 are preferred. The silver chloride layer can be formed on the silver meal layer by electrolytic oxidation of the surface layer of the silver metal layer or the deposition of silver chloride.

Examples of the quaternary ammonium salts to be used as the component for the ion-selective membrane include tetraalkyl ammonium salts having long-chain alkyl groups such as trioctylmethylammonium chloride (e.g., Aliquat 336, tradename, manufactured by Aldrich Chemical, Inc.).

For the preparation of the chlorine ion-selective electrode according to the present invention, the ion-selective membrane can be formed in the following manner.

A quaternary ammonium salt and the specified hydrophobic organic polymer serving as a binder are dissolved in a solvent capable of dissolving both compounds to prepare a solution containing them at a proper concentration, and the solution is coated or sprayed on the surface of the silver chloride layer and dried.

Examples of the vinyl acetals include vinyl formal, vinyl acetal and vinyl butyral, among which vinyl butyral is preferred. Examples of the organic polymers include vinyl acetal homopolymer and copolymers of said monomer and other monomer or monomers copolymerizable therewith such as copolymer of vinyl butyral and vinyl alcohol, a copolymer of vinyl butyral and vinyl acetate, a copolymer of vinyl butyral, vinyl alcohol and vinyl acetate and a copolymer of vinyl butyral, vinyl alcohol, vinyl acetate and vinyl methyl ether.

Though there are no limitations with regard to the ratio of the monomers to be copolymerized, it is desirable that the copolymers contains at least 50 mol.% of vinyl butyral.

Copolymers with vinyl chloride may be used, but it is not preferred to use copolymers containing 40 mol. % or more of vinyl chloride.

When polyvinyl butyral is used, ethanol is preferably employed as the solvent.

The following examples further illustrate the present invention.

EXAMPLE

A solution having the following composition (a) was coated on the whole surface of the silver chloride layer and the engraved portion of the silver metal/silver chloride electrode film described in Japanese Patent Provisional Publication No. 58(1983)-156848 to provide a chlorine ion-selective membrane having dry thickness of 11 $\mu$m.

| Composition (a) | |
|---|---|
| Polyvinyl butyral 2000-L, manufactured by Denki Kagaku Kogyo K. K. Japan) | 1.0 g. |
| Trioctylmethylammonium chloride (Aliquat 336, tradename of Aldrich Chemical, Inc.) | 1.0 g. |
| Surfactant KF 945 (manufactured by Shinetsu Chemical Industry Co., Ltd., Japan) 10% methyl ethyl ketone solution | 0.4 ml |
| Ethanol | 7.0 g. |

Thus-obtained electrode in the form of a long film was cut into about 6 mm widths, and the measurement of potential was made using a yarn bridge (as described in Japanese Patent Provisional Publication No. 58(1983)-156848) and Microprocessor Ionolyzer model 901 (manufactured by Orion Corp.). The results are shown in Table 1.

Calibrate (manufactured by General Diagnostics) was used as a reference solution and the concentrations of shlorine ions were adjusted so as to provide three chlorine ion concentrations given in Table 1. Each value of potential is the average of twenty measurements at each level.

TABLE 1

| Chlorine ion concn. (meq/l) | 72 | 96 | 133 |
|---|---|---|---|
| Potential (mV) | +6.6 | +0.2 | −6.7 |
| CV (%) | 0.68 | 0.56 | 0.68 |

As shown in Table 1, there was obtained the good linear relationship between the logarithmic value of the chlorine ion concentration and potential with satisfactory reproducibility.

For the purpose of comparison, a solution having the composition (b) was coated on the surface of the silver metal/silver chloride electrode in a similar manner to that described above to provide a chlorine ion-selective electrode. Potential was measured using thus prepared electrode. The results are shown in Table 2.

| Composition (b) | |
|---|---|
| Vinyl chloride-vinyl acetate copolymer polymerization ratio 90:10 (VYNS manufactured by Union Carbide) | 1.0 g. |
| Trioctylmethylammonium chloride (Aliquat 336 manufactured by Aldrich Chemical, Inc.) | 0.6 g. |
| Ethanol | 7.0 g. |

TABLE 2

| Chlorine ion concn. | 72 | 96 | 133 |
|---|---|---|---|
| CV (%) | 1.89 | 2.06 | 2.05 |

Further, a solution having the composition (c) was used to prepare an ion-selective electrode and potential was measured. The results are shown in Table 3.

| Composition (c) | |
|---|---|
| Polyvinyl chloride | 1.0 g. |
| Trioctylmethylammonium chloride (Aliquat 336 manufactured by Aldrich Chemical) | 1.0 g. |
| Surfactant KF 945 (manufactured by Shinetsu Chemical Industry Co., Ltd.), 10% methyl ethyl ketone solution | 0.4 ml |
| Tetrahydrofuran | 13 g. |

TABLE 3

| Chlorine ion concn. (meq/l) | 72 | 96 | 133 |
|---|---|---|---|
| CV (%) | 1.86 | 1.45 | 0.99 |

Each of the above-described three kinds of the ion-selective electrodes was then used for measurement of potential differences at lapse of 30, 60, 90 and 120 seconds after spotting the liquid sample. For this purpose, the liquid sample having the ion concentration of 96 meq/l was used. The results are shown in Table 4.

TABLE 4

| | Time (sec.) | | | |
|---|---|---|---|---|
| Binder | 30 | 60 | 90 | 120 |
| Polyvinyl butyral | −0.1 | −0.2 | −0.2 | −0.2 (mV) |
| VYNS | −5.6 | −0.6 | +0.9 | +1.0 |
| Polyvinyl chloride | +1.9 | −0.2 | −0.4 | 0.0 |

The electrode prepared using polyvinyl butyral according to the present invention is superior to the other three cases (Comparison Examples) in that change of generated potential with time is small and a time required for stabilization is short, that is, the drift of potential is small.

The above-described three kinds of the ion-selective electrodes were tested to evaluate the interference of bromine ion by adding a given amount of sodium bromide to a solution to be measured. The results are shown in Table 5. It is apparent from Table 5 at a bromine ion concentration of 3 meq/l that when the copolymer VYNS or polyvinyl chloride is used as a hydrophobic polymer, potential is greatly shifted, while when polyvinyl butyral is used, a serious effect for practical use is not found. The value of potential is the average of five measurements.

TABLE 5

| Chlorine ion concn. | <96 meq/l> | |
|---|---|---|
| Bromine ion concn. | 0 meq/l | 3 meq/l |
| Polyvinyl butyral | +0.2 | −0.6 |
| VYNS | +0.7 | −18.8 |
| Polyvinyl chloride | +0.1 | −9.6 |

We claim:

1. In a process for the quantitative analysis of chlorine ion contained in a liquid sample by applying the liquid sample on the ion-selective membrane of an ion-selective electrode having a silver metal layer, a silver chloride layer and a chloride ion-selective membrane containing a hydrophobic organic polymer as a binder, and measuring a potential produced in the electrode, the improvement which comprises said hydrophobic organic polymer being a vinyl acetal polymer or a copolymer of a vinyl acetal and at least one monomer copolymerizable therewith.

2. The process of claim 1 wherein the vinyl acetal polymer is polyvinyl butyral.

3. The process of claim 1 wherein the vinyl acetal polymer is polyvinyl formal.

4. The process of claim 1 wherein the vinyl acetal polymer is polyvinyl acetal.

5. The process of claim 1 wherein said vinyl acetal polymer is a copolymer of vinyl acetal and vinyl monomer other than vinyl acetal and the vinyl acetal unit derived from the vinyl acetal is present in the polymer in an amount of at least 50 mol. %.

* * * * *